United States Patent [19]

Souza et al.

[11] Patent Number: 5,151,511

[45] Date of Patent: Sep. 29, 1992

[54] DNA ENCODING AVIAN GROWTH HORMONES

[75] Inventors: Lawrence M. Souza, Thousand Oaks; Thomas C. Boone, Newbury Park, both of Calif.

[73] Assignee: Amgen Inc., Thousand Oaks, Calif.

[21] Appl. No.: 148,110

[22] Filed: Jan. 27, 1988

Related U.S. Application Data

[60] Continuation of Ser. No. 690,463, Jan. 10, 1985, abandoned, which is a division of Ser. No. 529,879, Sep. 9, 1983, abandoned, which is a continuation-in-part of Ser. No. 418,846, Sep. 16, 1982, abandoned.

[51] Int. Cl.[5] .............................. C12N 15/18
[52] U.S. Cl. ..................... 536/27; 435/320.1
[58] Field of Search ............... 435/320, 317.1; 536/27

[56] References Cited

U.S. PATENT DOCUMENTS 4,440,859  4/1984  Rutler et al. ................ 435/69.1

FOREIGN PATENT DOCUMENTS 0046039  2/1982  European Pat. Off. ............. 435/68

OTHER PUBLICATIONS

Fung et al., Nature, 307, 233–237 (1984).
Yang et al., Cell, 47, 3–10 (1986).
Foster et al., Biochem. Biophys. Res. Comm., 173(3), 967–975 (1990).
Tojo et al., Jap. J. Zoo Tech. Sci. 50, 863–869 (1979).
Broome et al. 1978 *PNAS* 75:2746–2749.
Goeddel et al. (1979) *Nature* vol. 281 pp. 544–548.
Seeburg et al. (1977) *Nature* vol. 270 pp. 486–494.
Suggs et al. (1981) *PNAS* vol. 78 pp. 6613–6617.
Farmer et al. (1974) *Endocrinology* vol. 95 pp. 1560–1565.
Miller et al. (1980) *J. Biological Chem.* vol. 255 pp. 7521–7524.
Crea et al. (1978) *Proc. Nat'l Acad Sci USA*, vol. 75 pp. 5765–5767.

*Primary Examiner*—Richard A. Schwartz
*Attorney, Agent, or Firm*—Marshall, O'Toole, Gerstein, Murray & Bicknell

[57] ABSTRACT

Novel polypeptides possessing biochemical and immunological properties of avian growth hormone are obtained by practice of recombinant DNA procedures. Novel DNA sequences are disclosed which are capable of directing the synthesis of such polypeptides in selected host microorganisms. In a preferred embodiment, a novel polypeptide with the properties of avian growth hormone of chicken species origins is produced as a result of bacterial expression of a novel plasmid, cGH-T21. This plasmid is harbored in transformed *E. coli* C600 cells deposited as A.T.C.C. 39182. Also disclosed is a DNA sequence capable of directing the synthesis of a novel polypeptide with the properties of avian growth hormone of turkey species origin.

2 Claims, No Drawings

DNA ENCODING AVIAN GROWTH HORMONES

This application is a continuation of application Ser. No. 690,463, filed Jan. 10, 1985, now abandoned, which is a division of application Ser. No. 529,879, filed Sep. 9, 1983, now abandoned, which is a continuation-in-part of application Ser. No. 418,846, filed Sep. 16, 1982, now abandoned.

BACKGROUND

The present invention relates generally to the manipulation of genetic materials and, more particularly to the use of recombinant procedures to secure the production of polypeptides possessing one or more biochemical and immunological properties of growth hormones of avian species.

A. Manipulation Of Genetic Materials

Genetic materials may be broadly defined as those chemical substances which program for and guide the manufacture of constituents of cells and viruses and direct the responses of cells and viruses. A long chain polymeric substance known as deoxyribonucleic acid (DNA) comprises the genetic material of all living cells and viruses except for certain viruses which are programmed by ribonucleic acids (RNA). The repeating units in DNA polymers are four different nucleotides, each of which consists of either a purine (adenine or guanine) or a pyrimidine (thymine or cytosine) bound to a deoxyribose sugar to which a phosphate group is attached. Attachment of nucleotides in linear polymeric form is by means of fusion of the 5' phosphate of one nucleotide to the 3' hydroxyl group of another. Functional DNA occurs in the form of stable double stranded associations of single strands of nucleotides (known as deoxyoligonucleotides), which associations occur by means of hydrogen bonding between purine and pyrimidine bases [i.e., "complementary" associations existing either between adenine (A) and thymine (T) or guanine (G) and cytosine (C)]. By convention, nucleotides are referred to by the names of their constituent purine or pyrimidine bases, and the complementary associations of nucleotides in double stranded DNA (i.e., A-T and G-C) are referred to as "base pairs". Ribonucleic acid is a polynucleotide comprising adenine, guanine, cytosine and uracil (U), rather than thymine, bound to ribose and a phosphate group.

Most briefly put, the programming function of DNA is generally effected through a process wherein specific DNA nucleotide sequences (genes) are "transcribed" into relatively unstable messenger RNA (mRNA) polymers. The mRNA, in turn, serves as a template for the formation of structural, regulatory and catalytic proteins from amino acids. This mRNA "translation" process involves the operations of small RNA strands (tRNA) which transport and align individual amino acids along the mRNA strand to allow for formation of polypeptides in proper amino acid sequences. The mRNA "message", derived from DNA and providing the basis for the tRNA supply and orientation of any given one of the twenty amino acids for polypeptide "expression", is in the form of triplet "condons"—sequential groupings of three nucleotide bases. In one sense, the formation of a protein is the ultimate form of "expression" of the programmed genetic message provided by the nucleotide sequence of a gene.

"Promoter" DNA sequences usually "precede" a gene in a DNA polymer and provide a site for initiation of the transcription into mRNA. "Regulator" DNA sequences, also usually "upstream" of (i.e., preceding) a gene in a given DNA polymer, bind proteins that determine the frequency (or rate) of transcription initiation. Collectively referred to as "promoter/regulator" or "control" DNA sequence, these sequences which precede a selected gene (or series of genes) in a functional DNA polymer cooperate to determine whether the transcription (and eventual expression) of a gene will occur. DNA sequences which "follow" a gene a in DNA polymer and provide a signal for termination of the transcription into mRNA are referred to as transcription "terminator" sequences.

A focus of microbiological processing for nearly the last decade has been the attempt to manufacture industrially and pharmaceutically significant substances using organisms which do not initially have genetically coded information concerning the desired product included in their DNA. Simply put, a gene that specifies the structure of a product is either isolated from a "donor" organism or chemically synthesized and then stably introduced into another organism which is preferably a self-replicating unicellular microorganism. Once this is done, the existing machinery for gene expression in the "transformed" host cells operates to construct the desired product.

The art is rich in patent and literature publications relating to "recombinant DNA" methodologies for the isolation, synthesis, purification and amplification of genetic materials for use in the transformation of selected host organisms. U.S. Pat. No. 4,237,224 to Cohen, et al., for example, relates to transformation of procaryotic unicellular host organisms with "hybrid" viral or circular plasmid DNA which includes selected exogenous DNA sequences. The procedures of the Cohen, et al. patent first involve manufacture of a transformation vector by enzymatically cleaving viral or circular plasmid DNA to form linear DNA strands. Selected foreign ("exogenous" or "heterologous") DNA strands are also prepared in linear form through use of similar enzymes. The linear viral or plasmid DNA is incubated with the foreign DNA in the presence of ligating enzymes capable of effecting a restoration process and "hybrid" vectors are formed which include the selected foreign DNA segment "spliced" into the viral or circular DNA plasmid.

Transformation of compatible unicellular host organisms with the hybrid vector results in the formation of multiple copies of the foreign DNA in the host cell population. In some instances, the desired result is simply the amplification of the foreign DNA and the "product" harvested is DNA. More frequently, the goal of transformation is the expression by the host cells of the foreign DNA in the form of large scale synthesis of isolatable quantities of commercially significant protein or polypeptide fragments coded for by the foreign DNA. See also, e.g., U.S. Pat. Nos. 4,269,731 (to Shine), 4,273,875 (to Manis) and 4,293,652 (to Cohen).

The development of specific DNA sequences for splicing into DNA vectors is accomplished by a variety of techniques, depending to a great deal on the degree of "foreignness" of the "donor" to the projected host and the size of the polypeptide to be expressed in the host. At the risk of oversimplification, it can be stated that three alternative principal methods can be employed: (1) the straightforward "isolation" of a double-stranded DNA sequence from donor DNA; (2) the chemical manufacture of a DNA sequence providing a code for a polypeptide of interest; and (3) the in vitro synthesis of a double-stranded DNA sequence by "reverse transcription" of mRNA isolated from donor cells. The last-mentioned methods, which involve formation of a DNA "complement" of mRNA are generally referred to as "cDNA" methods.

The success of procedures such as described in the Cohen, et al. patent is due in large part to the ready availability of "restriction endonuclease" enzymes which facilitate the site-specific cleavage of both the unhybridized DNA vector and, e.g., eukaryotic DNA strands containing the foreign sequences of interest. Cleavage in a manner providing for the formation of single stranded complementary "ends" on the double stranded linear DNA strands greatly enhances the likelihood of functional incorporation of the foreign DNA into the vector upon "ligating" enzyme treatment. A large number of such restriction endonuclease enzymes are currently commercially available [See, e.g., "BRL Restriction Endonuclease Reference Chart" appearing in the "'81/'82 Catalog" of Bethesda Research Laboratories, Inc., Gaithersburg, Md.]. Verification of hybrid formation is facilitated by chromatographic techniques which can, for example, distinguish the hybrid plasmids from non-hybrids on the basis of molecular weight. Other useful verification techniques involve radioactive DNA hybridization.

Successful expression of an exogenous gene in a transformed host microorganism depends to a great extent on incorporation of the gene into a transformation vector with a suitable promoter/regulator region present to insure transcription of the gene into mRNA and other signals which insure translation of the mRNA message into protein (e.g., ribosome binding sites). It is not often the case that the "original" promoter/regulator region of a structural gene as might be present in a donor cell will allow for high levels of expression in the new host. Consequently, the gene to be inserted in a DNA vector must either be fitted with a new, host-accommodated transcription and translation regulating DNA sequence prior to insertion or it must be inserted at a site where it will come under the control of existing transcription and translation signals in the vector DNA.

B. Growth Hormone as a Polypeptide of Interest

The terms, "growth hormone" and "somatotropin" are generically employed to designate hormonally active polypeptides secreted by the anterior lobe of pituitary glands of a variety of vertebrate species. In all species, the growth hormones function generally to regulate the rate of skeletal growth and gain in body weight. Hypophyseal dysfunction and consequent variations in growth hormone production have been associated with growth abnormalities such as giantism and dwarfism.

Significant research efforts have been devoted to the isolation and characterization of mammalian species growth hormones, for the purposes of human therapy and animal husbandry. One of the most exhaustively studied growth hormones has been bovine growth hormone (bGH). The complete, 191 amino acid sequence of bGH has been determined and recombinant methods have been employed to clone and sequence cDNA sequences coding for bGH and its precursor polypeptide form which includes a 26 amino acid "signal" or "leader" sequence which is cellularly deleted prior to entry of the hormone into circulation. See, e.g., Miller, et al., *J.Biol.Chem.*, 255, pp. 7521–7523 (1980). In a like manner, the structural gene coding for rat growth hormone (rGH) has been developed by cDNA methodologies, cloned, amplified and sequenced. See, e.g., Seeburg, et al., *Nature*, 270, pp. 485–494 (1977).

Prior to the cDNA work of Seeburg, et al., the precise total sequence of amino acids in natural or "native" rat growth hormone had not been determined. Based on analysis of nucleotides in the cloned cDNA, the sequence of bases in the mRNA was derived. This, in turn, allowed the determination of the sequence of amino acids in the rGH polypeptide. Rigorously speaking, such "determination" of rGH polypeptide sequence would more accurately be characterized as a "prediction" since it does not involve amino acid sequencing performed on isolated native growth hormone. When one considers the evidence supporting the accuracy of the prediction (the cellular origins of the mRNA, the similarities of predicted sequences to those determined by partial hydrolysis of native hormone and the like) the prediction takes on aspects of scientifically-determined fact. In this and similar circumstances, complete "verification" of the predicted polypeptide sequence as identical to that of the previously incompletely sequenced native substance will ordinarily be had upon finding that the polypeptide product of microbial expression of the cDNA possesses the biochemical and immunological properties of the native substance.

Comparatively little research effort has been directed to the study of avian growth hormones, with the result that their exact physical characteristics (molecular weights, amino acid sequences, and the like) are largely unknown.

Growth hormone isolated from the pituitaries of four avian species (chicken, duck, pigeon, and turkey) were examined by the bioassay and immunochemical techniques that proved successful in prior analyses of mammalian growth hormone in Farmer, et al., *J. Endocrin.*, 95, pp. 1560–1565 (1974). Amino acid sequencing analyses performed on the growth hormones revealed that the first four N-terminal amino acid residues for the duck and pigeon growth hormones were $NH_2$-Phe-Pro-Ala-Met. No sequences could be established for chicken and turkey growth hormones; however, the results of immunochemical tests indicated considerable relatedness between avian and mammalian growth hormones. See also, Harvey, et al., *J. Endocrin.*, 73, pp. 321–329 (1977). The high degree of similarity in amino acid composition (as determined by hydrolysis) and in biological and immunological activities of chicken, turkey, pigeon and duck growth hormone isolates is indicative of the likelihood that differences in amino acid sequences of growth hormones of various avian species are likely to be quite few in number. Thus, while reference is made in the literature to "chicken growth hormone", this is ordinarily in the context of designating the particular species source of the compound under investigation rather than structurally or chemically distinguishing the compound from that of another avian species.

More recent studies of the biochemical and immunological properties of avian growth hormone indicate that a high plasma level of growth hormone in young birds is at least partially responsible for their high growth rate. The secretion of growth hormone in young chickens is found to be very unstable and affected by stressful stimuli. Normally high circulating concentrations of growth hormone in young chickens are depressed by anesthesia, cold stress, infection, and certain other hormones, the release of which would be expected to be increased during stress. The plasma concentration of growth hormone in young birds is also affected by metabolic and nutritional factors. Under conditions of nutritional deprivation, growth hormone exerts a metabolic role, decreasing energy flow into lipids. It is also noted that circulating levels of growth hormone rise at the beginning of egg production in both turkeys and chickens. Growth hormone is considered to be involved in alleviating the metabolic load which the production of yolky eggs puts on the female bird. Scanes, et al., *Life Sciences*, 28, pp. 2895-2902 (1981). There thus appears to be a significant commercial potential for purified and isolated avian growth hormones in a variety of animal husbandry practices relating to production of commercial poultry products.

The isolation of avian growth hormones is presently conducted by fractional purification of extracts from either pituitaries of the avian species, or from avian plasma containing circulating growth hormone. Both procedures provide very small amounts of impure polypeptide substances. Avian growth hormones, including growth hormone specifically isolatable from domesticated chickens, have not heretofore been completely sequenced and, even if the sequence were completely determined, the application of the presently available methods for the chemical synthesis of entire polypeptides of nearly two hundred amino acids would likely provide exceedingly low yields at very high cost.

Thus, while information concerning some of the chemical and biological properties of avian growth hormones is known, the art has not been provided with any certain means for obtaining pure preparations of avian growth hormones in significant quantity. Further, recombinant DNA techniques have not been brought to bear in attempting to supply avian growth hormones.

BRIEF SUMMARY

According to the present invention, recombinant DNA techniques have for the first time been brought to bear to effect the quantitative microbial synthesis of polypeptide substances having the biochemical and immunological properties of avian growth hormones.

The achievement of this result initially involved the in vitro synthesis, determination of nucleotide sequence and amplification in bacteria of a structural gene sequences for an avian growth hormone starting with mRNA isolated from chicken and turkey pituitary cells. Also involved was the development of a hybrid DNA vector wherein the structural gene for avian growth hormone of chicken cell origins is operatively associated with a promoter/regulator DNA sequence allowing for the direct expression, by transformed microorganism host cells, of the desired polypeptide.

According to one of its aspects, the present invention provides polypeptides characterized by including part or all of the following amino acid sequence (commencing at the amino terminal):

| 1 | | | | | | | | | 10 | | | | |
|---|---|---|---|---|---|---|---|---|---|---|---|---|---|
| Thr | Phe | Pro | Ala | Met | Pro | Leu | Ser | Asn | Leu | Phe | Ala | Asn | Ala |
| Val | Leu | Arg | Ala | Gln | 20 His | Leu | His | Leu | Leu | Ala | Ala | Glu | Thr |
| Tyr | 30 Lys | Glu | Phe | Glu | Arg | Thr | Tyr | Ile | Pro | Glu | 40 Asp | Gln | Arg |
| Tyr | Thr | Asn | Lys | Asn | Ser | Gln | 50 Ala | Ala | Phe | Cys | Tyr | Ser | Glu |
| Thr | Ile | Pro | 60 Ala | Pro | Thr | Gly | Lys | Asp | Asp | Ala | Gln | Gln | 70 Lys |
| Ser | Asp | Met | Glu | Leu | Leu | Arg | Phe | Ser | 80 Leu | Val | Leu | Ile | Gln |
| Ser | Trp | Leu | Thr | Pro | 90 Val | Gln | Tyr | Leu | Ser | Lys | Val | Phe | Thr |
| Asn | 100 Asn | Leu | Val | Phe | Gly | Thr | Ser | Asp | Arg | Val | 110 Phe | Glu | Lys |
| Leu | Lys | Asp | Leu | Glu | Glu | Gly | 120 Ile | Gln | Ala | Leu | Met | Arg | Glu |
| Leu | Glu | Asp | 130 Arg | Ser | Pro | Arg | Gly | Pro | Gln | Leu | Leu | Arg | 140 Pro |
| Thr | Tyr | Asp | Lys | Phe | Asp | Ile | His | Leu | 150 Arg | Asn | Glu | Asp | Ala |
| Leu | Leu | Lys | Asn | Tyr | 160 Gly | Leu | Leu | Ser | Cys | Phe | Lys | Lys | Asp |
| Leu | 170 His | Lys | Val | Glu | Thr | Tyr | Leu | Lys | Val | Met | 180 Lys | Cys | Arg |
| Arg | Phe | Gly | Glu | Ser | Asn | Cys | 190 Thr | 191 Ile. | | | | | |

The above-characterized polypeptide conforms with published fragmentary sequences for avian growth hormone and [Met$^{-1}$,des-Thr$^1$] form possesses demonstrable avian growth hormone biochemical and immunological properties in competition assays wherein it selectively competes with ovine growth hormone for antigen-antibody complex formation with anti-ovine growth hormone antibody. It is thus verified as being an avian growth hormone, and specifically avian growth hormone native to chickens.

According to another of its aspects, the present invention provides polypeptides characterized by including part or all of the following amino acid sequence (commencing at its amino terminal):

| 1   |     |     |     |     |     |     |     |     | 10  |     |     |     |
|-----|-----|-----|-----|-----|-----|-----|-----|-----|-----|-----|-----|-----|
| Thr | Phe | Pro | Thr | Met | Pro | Leu | Ser | Asn | Leu | Phe | Thr | Asn | Ala |

|     |     |     |     |     | 20  |     |     |     |     |     |     |     |     |
| Val | Leu | Arg | Ala | Gln | His | Leu | His | Leu | Leu | Ala | Ala | Glu | Thr |

|     | 30  |     |     |     |     |     |     |     |     | 40  |     |     |
| Tyr | Lys | Glu | Phe | Glu | Arg | Thr | Tyr | Ile | Pro | Glu | Asp | Gln | Arg |

|     |     |     |     |     |     |     | 50  |     |     |     |     |     |
| Tyr | Thr | Asn | Lys | Asn | Ser | Gln | Ala | Ala | Phe | Cys | Tyr | Ser | Glu |

|     |     |     | 60  |     |     |     |     |     |     |     |     | 70  |
| Thr | Ile | Pro | Ala | Pro | Thr | Gly | Lys | Asp | Asp | Ala | Gln | Gln | Lys |

|     |     |     |     |     |     |     |     | 80  |     |     |     |     |
| Ser | Asp | Met | Glu | Leu | Leu | Arg | Phe | Ser | Leu | Val | Leu | Ile | Gln |

|     |     |     |     |     | 90  |     |     |     |     |     |     |     |
| Ser | Trp | Leu | Thr | Pro | Met | Gln | Tyr | Leu | Ser | Lys | Val | Phe | Thr |

|     | 100 |     |     |     |     |     |     |     |     | 110 |     |     |
| Asn | Asn | Leu | Val | Phe | Gly | Thr | Ser | Asp | Arg | Val | Phe | Glu | Lys |

|     |     |     |     |     |     | 120 |     |     |     |     |     |     |
| Leu | Lys | Asp | Leu | Glu | Glu | Gly | Ile | Gln | Ala | Leu | Met | Arg | Glu |

|     |     | 130 |     |     |     |     |     |     |     |     |     | 140 |
| Leu | Glu | Asp | Arg | Ser | Pro | Arg | Gly | Pro | Gln | Leu | Leu | Arg | Pro |

|     |     |     |     |     |     |     |     | 150 |     |     |     |     |
| Thr | Tyr | Asp | Arg | Phe | Asp | Ile | His | Leu | Arg | Ser | Glu | Asp | Ala |

|     |     |     |     |     | 160 |     |     |     |     |     |     |     |
| Leu | Leu | Lys | Asn | Tyr | Gly | Leu | Leu | Ser | Cys | Phe | Lys | Lys | Asp |

|     | 170 |     |     |     |     |     |     |     |     |     | 180 |     |
| Leu | His | Lys | Val | Glu | Thr | Tyr | Leu | Lys | Val | Met | Lys | Cys | Arg |

|     |     |     |     |     |     | 190 | 191 |
| Arg | Phe | Gly | Glu | Ser | Asn | Cys | Asp | Ile. |

The above-described sequence also conforms with sparse published data on avian growth hormone, and is specifically an amino acid sequence for avian growth hormone native to the turkey species.

The above amino acid sequences for avian growth hormones of the type native to chicken and turkey species may be directly expressed by selected host microorganisms with an initial methionine residue at the amino terminal, i.e., as the [Met⁻¹] analog of the mature polypeptide or expressed as a portion of a fusion protein from which they may be isolated by selective cleavage. They may also be directly expressed with an approximately 25 amino acid "leader" region, set out below, which is duplicative of a leader region synthesized in avian (chicken and turkey) pituitary cells and which is apparently processed off of the mature polypeptide prior to entry of the growth hormone into circulation.

or growth-inducing agents useful in treating and raising fowl, especially chickens and turkeys, or other animals. The polypeptides also provide a large and reliably-produced quantity of pure avian growth hormone substances useful in the development of information concerning avian metabolism. As an example, purified and isolated polypeptides of the invention are expected to be highly useful in immunological determinations wherein they may serve as readily quantified antigens or stimulants for the development of specific antibodies to avian growth hormones.

Polypeptides of the invention are produced in quantity by recombinant methods wherein selected host cells, preferably of a microorganism such as E. coli or yeast, are transformed with a hybrid viral or plasmid DNA vector including a specific DNA sequence coding for the polypeptide or polypeptide analog and the polypeptide is synthesized in the host upon transcription and translation of the DNA sequence. According to another of its aspects, therefore, the present invention provides purified and isolated continuous, double-stranded DNA sequences capable of directing the synthesis in a selected host microorganism of a polypeptide possessing one or more of the biochemical and immunological properties of an avian growth hormone. Two

|             |     |     |     |     |     | −20 |     |     |     |     |     |     |     |
|-------------|-----|-----|-----|-----|-----|-----|-----|-----|-----|-----|-----|-----|-----|
| NH₂—Met     | Ala | Pro | Gly | Ser | Trp | Phe | Ser | Pro | Leu | Leu | Ile | Ala |     |
|             | −10 |     |     |     |     |     |     |     |     | −1  |     |     |     |
| Val Val     | Thr | Leu | Gly | Leu | Pro | Gln | Glu | Ala | Ala | Ala—[mature |     |     |
| polypeptide sequence] |

Polypeptides provided by the present invention may suitably be employed in the manufacture of therapeutic illustrative DNA sequences of the invention include the following sequence of nucleotide bases in the top strand thereof,

```
5'- ACC TTC CCT GCC ATG CCC CTC TCC AAC CTG TTT GCC AAC
GCT GTG CTG AGG GCT CAG CAC CTC CAC CTC CTG GCT GCC GAG
ACA TAT AAA GAG TTC GAA CGC ACC TAT ATT CCG GAG GAC CAG
AGG TAC ACC AAC AAA AAC TCC CAG GCT GCG TTT TGT TAC TCA
GAA ACC ATC CCA GCT CCC ACG GGG AAG GAT GAC GCC CAG CAG
AAG TCA GAC ATG GAG CTG CTT CGG TTT TCA CTG GTT CTC ATC
CAG TCC TGG CTC ACC CCC GTG CAA TAC CTA AGC AAG GTG TTC
ACG AAC AAC TTG GTT TTT GGC ACC TCA GAC AGA GTG TTT GAG
AAA CTA AAG GAC CTG GAA GAA GGG ATC CAA GCC CTG ATG AGG
GAG CTG GAG GAC CGC AGC CCG CGG GGC CCG CAG CTC CTC AGA
CCC ACC TAC GAC AAG TTC GAC ATC CAC CTG CGC AAC GAG GAC
GCC CTG CTG AAG AAC TAC GGC CTG CTG TCC TGC TTC AAG AAG
GAT CTG CAC AAG GTG GAG ACC TAC CTG AAG GTG ATG AAG TGC
CGG CGC TTC GGA GAG AGC AAC TGC ACC ATC-3';
``` and

```
5'- ACC TTC CCT ACC ATG CCC CTC TCC AAC CTG TTC ACC AAC
GCT GTG CTG AGG GCT CAG CAC CTC CAC CTC CTG GCT GCT GAG
ACA TAC AAA GAG TTC GAA CGC ACC TAT ATT CCG GAG GAC CAG
AGG TAC ACC AAC AAA AAC TCC CAG GCT GCA TTT TGT TAC TCA
GAA ACC ATC CCA GCT CCC ACA GGG AAG GAT GAT GCC CAG CAG
AAA TCG GAC ATG GAG CTG CTT CGG TTT TCA CTG GTT CTC ATC
CAG TCC TGG CTG ACC CCC ATG CAA TAC CTA AGC AAG GTG TTC
ACA AAC AAT TTG GTT TTC GGC ACC TCA GAC AGA GTG TTT GAG
AAA CTA AAG GAC CTG GAA GAA GGG ATC CAA GCC CTG ATG AGG
GAG TTG GAG GAT CGC AGC CCG CGG GGC CCG CAG CTC CTC AGA
CCC ACC TAC GAC AGG TTC GAC ATC CAC CTG CGC AGC GAG GAC
GCC CTG CTG AAG AAC TAC GGC TTG CTG TCC TGC TTC AAG AAG
GAC CTG CAC AAA GTG GAG ACC TAC CTG AAG GTG ATG AAG TGC
CGG CGC TTC GGG GAG AGC AAC TGC AAC ATC-3'.
```

The above-specified DNA sequences for avian growth hormone polypeptides may be incorporated into a vector in association with a DNA sequence coding for an amino acid leader sequence such as is apparently present in "precursor" polypeptides formed in avian pituitary cells, and/or with 5' and 3' untranslated sequences. These sequences on either side of the protein-coding DNA sequence may be employed to supply unique endonuclease enzyme restriction sites to facilitate insertion into a selected vector. As an example, part or all of the following 5' untranslated DNA sequence and leader sequence may be employed 5' to the codon for the initial amino acid in one of the avian growth hormone sequences above:

```
5'-ACCTGGATGAAAGGAGGAAACGTTCAACACCTGAGCAACTCTCCCGGCAGGA
-25                          -20
Met Ala Pro Gly Ser Trp Phe Ser Pro Leu Leu Ile Ala Val
ATG GCT CCA GGC TCG TGG TTT TCT CCT CTC CTC ATC GCT GTG

-10                                      -1
Val Thr Leu Gly Leu Pro Gln Glu Ala Ala Ala
GTC ACG CTG GGA CTG CCG CAG GAA GCT GCT GCC-3'.
```

Similarly, one or more transcription stop codons or part or all of the "naturally occurring" 3' untranslated DNA sequences may be employed 3' to the codon for the carboxy terminal (Ile[191]) amino acid.

The above-specified DNA sequences, by virtue of their cDNA origins (i.e., by virtue of development as a complement to chicken growth hormone mRNA and turkey growth hormone mRNA, respectively), comprise DNA triplet codons especially suited for high level expression of growth hormone in avian cells. When polypeptide expression in microorganisms such as bacteria and yeast is to be achieved, it may be desirable that a part or the entirety of the sequences be substituted with a sequence of bases arranged into codons which are the subject of preferred translation by the projected host. The invention thus comprehends the above-specified sequences and alternative sequences of nucleotide bases comprising triplet codons specifying polypeptides with the same sequence of amino acids.

A specific aspect of the invention, therefore, is the provision of DNA sequences which code for polypeptides displaying the biochemical and immunological properties of avian growth hormone and which comprise nucleotides arranged entirely or in part according to such codon usages as are endogenous to avian cells and/or entirely or in part according to codons noted to be the subject of preferred or "optimal" expression in microorganisms. One such composite or "hybird" sequence of the invention includes a cDNA-derived duplicate of a chicken growth hormone nucleotide sequence wherein approximately 32 of the initial codons (commencing at the 5' end of the polypeptide coding region) are replaced and supplemented by the following manufactured DNA sequence:

```
                   1                  2           3           4
        Xbal       0    Thr           0           0           0
    5' C TAG AGA ATG ACC TTT CCA GCT ATG CCT CTG TCT AAT CTG
    3'         TCT TAC TGG AAA GGT CGA TAC GGA GAC AGA TTA GAC
```

```
              50                 60                  70              80
         TTT GCA AAC GCT GTT CTG CGT GCA CAG CAT CTG CAT CTG CTG
         AAA CGT TTG CGA CAA GAC GCA CGT GTC GTA GAC GTA GAC GAC 90                 100
         GCC GCT GAA ACT TAT AAA GAA TT 3'
         CGG CGA CTT TGA ATA TTT CTT AAGC 5'
                                        TaqI
```

This exemplary composite sequence is seen to provide various features making it especially useful in securing microbial expression of polypeptides of the invention in that its manufactured portion includes: a base codon specifying an initial methionine (base pair numbers 8–10); base codons optimally expressed in bacteria; and bases facilitating use of readily available restriction endonucleases in the formation of hybrid transformation vectors (an XbaI "sticky end"). DNA sequences of the invention may also be entirely manufactured (and substantially include only host-preferred codons) according to the synthetic methods of co-owned, co-pending U.S. patent application Ser. Nos. 375,494 (filed May 6, 1982) and 483,451 (filed Apr. 15, 1983) by Alton, et al.

In preferred embodiments, the DNA sequences of the invention are inserted into microorganism transformation vectors such as self-replicating, selectable plasmids derived from E. coli plasmid pBR322. The hybrid plasmids are employed to transform suitable host microorganisms, such as E. coli K-12. The transformation vectors, in addition to including the DNA sequence capable of directing the synthesis of a polypeptide possessing one or more of the biochemical and immunological properties of avian growth hormone, additionally may comprise natural or synthetic transcription promotor/regulator DNA sequences 5' to the polypeptide coding region.

Comprehended by the present invention, therefore, is the novel method for manufacturing an avian growth hormone polypeptide substance comprising: (1) transforming a selected microorganism with a transformation vector including a DNA sequence capable of directing microorganism synthesis of a polypeptide possessing one or more of the biochemical and immunological properties of avian growth hormone; (2) growing microorganisms so transformed under suitable nutrient conditions; and, (3) isolating from said microorganisms the product of the expression of said DNA sequence therein.

A DNA vector, designated cGH-T21, suitable for use in practice of the invention to stably transform bacterial cells and to thereby allow for the expression therein of readily isolatable quantities of a polypeptides according to the invention has been deposited with the American Type Culture Collection, Rockville, Md. The plasmid vector is harbored in a collection of E. coli C600 cells given A.T.C.C. deposit No. 39182.

Further aspects and advantages of the present invention will be apparent upon consideration of the following detailed description of the practice of preferred embodiments thereof.

DETAILED DESCRIPTION

According to the present invention, a high molecular weight polypeptide having the biochemical and immunological properties of avian growth hormone native to the chicken species has been produced in isolatable quantities in cells other than those of functional avian pituitary tissue. These results were obtained by a series of recombinant DNA manipulative procedures involving, inter alia, the isolation of messenger RNA from chicken pituitary tissue; the selection of avian growth hormone-generating forms of mPNA from the isolated RNA; the synthesis of a reverse transcript cDNA from the mRNA; the sequencing of the cDNA and derivation of an avian growth hormone amino acid sequence corresponding thereto; the construction of an illustrative bacterial cell expression vector, cGH-T21, harbored in A.T.C.C. No. 39182 which includes a replica of the cDNA; the transformation of cells with the vector to secure expression of the desired polypeptide; and, testing of polypeptide products of transformed cells. Also involved in the making of the present invention was the development of an illustrative, alternative DNA sequence including, in part, a manufactured DNA sequence including E. coli preference codons for the desired polypeptide; the development of an alternative expression vector allowing for higher levels of bacterial expression of desired polypeptides; and a series of manipulations performed on turkey pituitary tissue and resulting in isolation of cDNA for avian growth hormone of turkey species origins.

The following example is directed to isolation of messenger RNA from chicken pituitary glands.

EXAMPLE 1

Chicken pituitary glands were extracted from one-year-old spent hens and immediately frozen in liquid nitrogen. Approximately 0.4 grams of chicken pituitary (roughly 40–50 pituitaries) were extracted using the guanidinium thiocynate procedure for the quantitative isolation of intact RNA. [Chirgwin, et al., *Biochemistry*, 18, pp. 5294–5299 (1979)].

Briefly, the Chirgwin, et al. procedure involves homogenizing the chicken pituitaries in a stock solution of guanidinium thiocynate, a strong denaturant. The homogenates are centrifuged to sediment particulate material and the supernates are mixed with acetic acid and incubated to precipitate the nucleic acid. The material is then centrifuged and the resulting pellet resuspended in guanidine hydrochloride stock solution. The RNA is re-precipitated in solution with acetic acid and ethanol, incubated, and centrifuged. After a final re-precipitation from guanidine hydrochloride, the re-precipitated material is centrifuged again and the pellets dispersed in ethanol at room temperature. Following centrifugation, the ethanol is removed from the pellet by a stream of nitrogen and the RNA dissolved in sterile water. The RNA is reprecipitated with sodium acetate (pH 7.0) and ethanol. RNA is sedimented from the ethanol suspension by centrifugation, the pellets thoroughly washed with ethanol, dried with nitrogen, and dissolved again in sterile water.

The final solution in sterile water contains the purified extracts of total RNA from the chicken pituitaries. To obtain only the messenger RNA from the total RNA solution, the RNA solution is passed through a column containing oligodeoxythymidylate [oligo (dT)] (Collaborative Research, Inc.). The poly-adenylated (poly-A+) tails characteristic of messenger RNA adhere to the column while ribosomal RNA is discarded in the eluate. Following this procedure, 16 µg of polyadenylated messenger RNA (poly-A+ mRNA) are isolated.

The following example is directed to construction of cDNA clones from the messenger RNA isolated in Example 1.

EXAMPLE 2

Prior to its use in the cDNA synthesis procedure of Okayama, et al., *Molecular & Cellular Biology*, 2, pp. 161-170 (1982), the poly-A+ messenger RNA isolated in Example 1 was pre-treated with methylmercury hydroxide (Alpha Ventron) at a final concentration of 4 mM for 5 minutes at room temperature. The methylmercury hydroxide treatment denatures interactions of messenger RNA, both with itself and with contaminating molecules that inhibit translation. See, Payvar, et al., *J.Biol.Chem.*, 258, pp. 7636-7642 (1979).

Briefly described, the Okayama procedure involves the following steps: A vector primer is prepared by digesting the plasmid recombinant pBR322-SV40 (map units 0.71-0.86) (Paul Berg, Ph. D., Stanford University) with KpnI (Bethesda Research Labs) endonuclease which cuts the circular plasmid at one site. After the DNA is extracted, deoxythymidylate (dT) residues are added to the KpnI endonuclease generated termini of the plasmid with calf thymus terminal deoxynucleotidyl transferase (Enzo Biochemicals). The DNA, now having poly-T tails, is then digested with HpaI (Bethesda Research Labs) endonuclease which removes one poly-T tail. The large DNA fragment which contains the origin of pBR322 DNA replication and one poly-T tail is purified by agarose gel electrophoresis, and absorption and elution from an oligodeoxyadenylate [oligo (dA)] cellulose column (Collaborative Research, Inc.).

An oligodeoxyguanylate, [oligo (dG)]-tailed linker DNA is prepared by digesting pBR322-SV40 (map units 0.19-0.32) (Berg) with PstI endonuclease (AMGen) which cuts the circularized plasmid at two restriction sites, thereby generating a large DNA fragment and a small DNA fragment. Tails of deoxyguanylate residues are then added to each end of the two fragments, with terminal deoxynucleotidyl transferase. The extracted and precipitated DNA is then digested with HindIII endonuclease (Bethesda Research Labs), which cuts the restriction site on the smaller fragment creating two fragments of unequal size. The smallest oligo (dG)-tailed linker is then purified by agarose gel electrophoresis.

The first step in cDNA synthesis involves adding the methylmercury hydroxide-treated mRNA to the reverse transcription reaction, which contains 2-mercapto ethanol, Tris, magnesium chloride, $^{32}$P-$\alpha$-dCTP (New England Nuclear), reverse transcriptase (Life Sciences, Inc.), and vector primer. In this reaction, the plasmid vector DNA functions as the primer for the synthesis of the first cDNA strand. Annealing of the poly-A+ messenger RNA to the poly-dT-tailed vector DNA generates the substrate for reverse transcription of the mRNA sequence.

To generate a cohesive tail at the end of the cDNA so that it can be ligated to the other end of the vector primer DNA and thereby provide the template for second-strand DNA synthesis, the double-stranded plasmid-cDNA:mRNA from the reverse transcription reaction is added to a mixture containing $^{32}$P-$\alpha$-dCTP and terminal deoxynucleotidyl transferase. This step adds oligo (dC) tails to the 3' ends of the vector primer c-DNA hybrid. The pellet from the oligo (dC) addition reaction is then added to a reaction containing HindIII endonuclease. The HindIII endonuclease digestion removes the oligo (dC) tail from the vector primer DNA terminus by cleavage at the unique HindIII restriction site near that end. The mRNA:cDNA hybrid, being a very poor substrate for HindIII endonuclease, remains intact during digestion, with limiting quantities of the restriction enzyme.

The HindIII endonuclease digested oligo-(dC)-tailed cDNA:mRNA plasmid is incubated in a mixture containing the oligo (dG)-tailed linker DNA. Addition of *E.coli* ligase (New England Biology Labs) mediates cyclization by a covalent joining of the linker and vector DNAs via their HindIII cohesive ends and a noncovalent base paired join made to the cDNA:mRNA duplex via the oligo (dG) tail of the linker and to the oligo (dC) tail of the cDNA. The messenger RNA strand in the resulting double-stranded recombinant is replaced by DNA by reaction with *E.coli* RNaseH (PL Biochemical Co.), *E.coli* DNA ligase, *E.coli* DNA polymerase-1, and four deoxynucleoside triphosphates (Sigma). The RNaseH introduces nicks in the RNA strand, while Pol/I and the four deoxynucleoside triphosphates replace the RNA segments by nick translation. *E.coli* DNA ligase joins the newly-synthesized DNA fragments into a continuous second cDNA strand. In the repair synthesis, the oligo (dG) tail of linker DNA serves as the primer for copying any unpaired deoxyribosylcytidine (dC) sequence and extending the strand to the cDNA region.

Thus, the full or nearly full-length reverse transcript of the mRNAs are preferentially converted to duplex cDNAs. The cDNAs are then transformed by incubation into a host microorganism *E.coli* K-12 strain HB101 for amplification.

The following example is directed to isolation of chicken species avian growth hormone-coding (hereafter "cGH") clones by hybridization of pBR322-SV40 recombinants containing the cDNA sequence with a nick-translated probe comprising DNA fragments coding for bovine growth hormone and rat growth hormone, respectively.

EXAMPLE 3

The complexity of the mRNA isolated from chicken pituitaries necessitates screening a moderate number of recombinant clones containing cDNA inserts in order to locate the clone which codes for synthesis of a polypeptide having one or more of the biochemical and immunological properties of chicken growth hormone.

According to the procedure of Hanaban, et al., *Gene*, 10, 63-67 (1980), bacteria containing recombinants with cDNA inserts are spread on a nitrocellulose filter (Millipore) laid on a agar plate. The plate is then incubated to establish small colonies which are replicated to another nitrocellulose filter. The replicas are incubated until distinct colonies appear. The bacteria on the filters are lysed on sheets of Whatman 3 MM paper barely saturated with sodium hydroxide (0.5M). After blotting, the process is repeated again with sodium hydroxide, tris (1M), and tris (0.5M)-sodium chloride (1.5M). When the filters are nearly dry, they are baked for 2 hours at 80° C. in a vacuum oven prior to nucleic acid hybridization. [See Wahl, et al., *PNAS*, 76, pp. 3683–3687 (1979); and Maniatis, et al., *Cell*, 81, pp. 163–182 (1976)].

The recombinant clones obtained are hybridized with either a radiolabelled 490 base pair PvuII fragment from pBR322-bGH15 (a plasmid including a bovine growth hormone gene) or a radiolabelled 816 base pair fragment from pRGH-1 [Seeberg, et al, *Nature*, 270, p. 486 (1977)], a plasmid including a rat growth hormone gene. These plasmid fragments containing the bovine growth hormone DNA sequence and the rat growth hormone DNA sequence, respectively, when hybridized with the recombinants containing chicken pituitary cDNA inserts, detect the homologous chicken growth hormone DNA sequence. The probe fragments align with the corresponding cDNA chicken growth hormone sequence in several recombinants. Eight clones containing the cGH sequence were detected using autoradiography. The bacterial colonies on the original filter are thereby identified and selected to propagate additional copies of the cGH-containing recombinants.

Each clone digested with restriction endonucleases RsaI (New England Biology Labs), Eco RII (Bethesda Research Labs), and TagI (Bethesda Research Labs) revealed similar restriction endonuclease patterns. One clone, cGH5, was randomly selected for further characterization and sequence analysis.

The following example is directed to characterizing by sequence analysis a cGH-coding clone.

EXAMPLE 4

Sequencing of the recombinant cGH DNA obtained by the procedure of Example 3 was accomplished by the dideoxy method of Sanger, et al., *PNAS*, 74, pp. 5463–5467 (1977).

The single-stranded DNA phage M-13 was used as a cloning vector for supplying single-stranded DNA templates from the double-stranded cDNA clones. The Sanger, et al. method revealed the sequence for the cGH protein coding DNA single strand in M-13, which included the cGH coding region having a single BamHI recognition site; an approximately 75 base sequence 5' to the cGH coding region which sequence presumptively codes for a 25 amino acid leader region; and 3' and 5' untranslated regions. This sequence is set out in Table I below with its accompanying amino acid translation:

TABLE I

5'-ACCTGGATGAAAGGAGGAAACGTTCAAGCAACACCTGAGCAACTCTCCCGGCA

|     | -25 Met | Ala | Pro | Gly | Ser | -20 Trp | Phe | Ser | Pro | Leu | Leu | Ile | Ala |
|-----|-----|-----|-----|-----|-----|-----|-----|-----|-----|-----|-----|-----|-----|
| GGA | ATG | GCT | CCA | GGC | TCG | TGG | TTT | TCT | CCT | CTC | CTC | ATC | GCT |

|     | Val | Val | -10 Thr | Leu | Gly | Leu | Pro | Gln | Glu | Ala | Ala | 1 Ala | Thr | Phe |
|-----|-----|-----|-----|-----|-----|-----|-----|-----|-----|-----|-----|-----|-----|-----|
|     | GTG | GTC | ACG | CTG | GGA | CTG | CCG | CAG | GAA | GCT | GCT | GCC | ACC | TTC |

|     | Pro | Ala | Met | Pro | Leu | Ser | Asn | 10 Leu | Phe | Ala | Asn | Ala | Val | Leu |
|-----|-----|-----|-----|-----|-----|-----|-----|-----|-----|-----|-----|-----|-----|-----|
|     | CCT | GCC | ATG | CCC | CTC | TCC | AAC | CTG | TTT | GCC | AAC | GCT | GTG | CTG |

|     | Arg | Ala | Gln | 20 His | Leu | His | Leu | Leu | Ala | Ala | Glu | Thr | Tyr | 30 Lys |
|-----|-----|-----|-----|-----|-----|-----|-----|-----|-----|-----|-----|-----|-----|-----|
|     | AGG | GCT | CAG | CAC | CTC | CAC | CTC | CTG | GCT | GCC | GAG | ACA | TAT | AAA |

|     | Glu | Phe | Glu | Arg | Thr | Tyr | Ile | Pro | Glu | 40 Asp | Gln | Arg | Tyr | Thr |
|-----|-----|-----|-----|-----|-----|-----|-----|-----|-----|-----|-----|-----|-----|-----|
|     | GAG | TTC | GAA | CGC | ACC | TAT | ATT | CCG | GAG | GAC | CAG | AGG | TAC | ACC |

|     | Asn | Lys | Asn | Ser | Gln | 50 Ala | Ala | Phe | Cys | Tyr | Ser | Glu | Thr | Ile |
|-----|-----|-----|-----|-----|-----|-----|-----|-----|-----|-----|-----|-----|-----|-----|
|     | AAC | AAA | AAC | TCC | CAG | GCT | GCG | TTT | TGT | TAC | TCA | GAA | ACC | ATC |

|     | Pro | 60 Ala | Pro | Thr | Gly | Lys | Asp | Asp | Ala | Gln | Gln | 70 Lys | Ser | Asp |
|-----|-----|-----|-----|-----|-----|-----|-----|-----|-----|-----|-----|-----|-----|-----|
|     | CCA | GCT | CCC | ACG | GGG | AAG | GAT | GAC | GCC | CAG | CAG | AAG | TCA | GAC |

|     | Met | Glu | Leu | Leu | Arg | Phe | Ser | 80 Leu | Val | Leu | Ile | Gln | Ser | Trp |
|-----|-----|-----|-----|-----|-----|-----|-----|-----|-----|-----|-----|-----|-----|-----|
|     | ATG | GAG | CTG | CTT | CGG | TTT | TCA | CTG | GTT | CTC | ATC | CAG | TCC | TGG |

|     | Leu | Thr | Pro | 90 Val | Gln | Tyr | Leu | Ser | Lys | Val | Phe | Thr | Asn | 100 Asn |
|-----|-----|-----|-----|-----|-----|-----|-----|-----|-----|-----|-----|-----|-----|-----|
|     | CTC | ACC | CCC | GTG | CAA | TAC | CTA | AGC | AAG | GTG | TTC | ACG | AAC | AAC |

|     | Leu | Val | Phe | Gly | Thr | Ser | Asp | Arg | Val | 110 Phe | Glu | Lys | Leu | Lys |
|-----|-----|-----|-----|-----|-----|-----|-----|-----|-----|-----|-----|-----|-----|-----|
|     | TTG | GTT | TTT | GGC | ACC | TCA | GAC | AGA | GTG | TTT | GAG | AAA | CTA | AAG |

|     | Asp | Leu | Glu | Glu | Gly | 120 Ile | Gln | Ala | Leu | Met | Arg | Glu | Leu | Glu |
|-----|-----|-----|-----|-----|-----|-----|-----|-----|-----|-----|-----|-----|-----|-----|
|     | GAC | CTG | GAA | GAA | GGG | ATC BamHI | CAA | GCC | CTG | ATG | AGG | GAG | CTG | GAG |

|     | 130 Asp | Arg | Ser | Pro | Arg | Gly | Pro | Gln | Leu | Leu | Arg | 140 Pro | Thr | Tyr |
|-----|-----|-----|-----|-----|-----|-----|-----|-----|-----|-----|-----|-----|-----|-----|
|     | GAC | CGC | AGC | CCG | CGG | GGC | CCG | CAG | CTC | CTC | AGA | CCC | ACC | TAC |

TABLE I-continued

| | | | | | | | 150 | | | | | | |
|---|---|---|---|---|---|---|---|---|---|---|---|---|---|
| Asp | Lys | Phe | Asp | Ile | His | Leu | Arg | Asn | Glu | Asp | Ala | Leu | Leu |
| GAC | AAG | TTC | GAC | ATC | CAC | CTG | CGC | AAC | GAG | GAC | GCC | CTG | CTG |
| | | 160 | | | | | | | | | | 170 | |
| Lys | Asn | Tyr | Gly | Leu | Leu | Ser | Cys | Phe | Lys | Lys | Asp | Leu | His |
| AAG | AAC | TAC | GGC | CTG | CTG | TCC | TGC | TTC | AAG | AAG | GAT | CTG | CAC |
| | | | | | | | | 180 | | | | | |
| Lys | Val | Glu | Thr | Tyr | Leu | Lys | Val | Met | Lys | Cys | Arg | Arg | Phe |
| AAG | GTG | GAG | ACC | TAC | CTG | AAG | GTG | ATG | AAG | TGC | CGG | CGC | TTC |
| | | | | 190 | | | | | | | | | |
| Gly | Glu | Ser | Asn | Cys | Thr | Ile | OP | | | NcoI | | | |
| GGA | GAG | AGC | AAC | TGC | AAC | ATC | TGA | GGCCCTGTGCCTGCGCCATGG-3' | | | | | |

The above sequence is not readily susceptible for securing direct expression of cGH in a microbial host. To secure such expression the cGH coding region should be provided with an initial ATG codon and the sequence should be inserted in a transformation vector at a site under control of a suitable promoter/regulator DNA sequence. The following Example 5 relates to construction of an expression vector.

The following example is directed to constructing a plasmid expression vector, cGH-T21 harbored in A.T.C.C. 39182 cells.

EXAMPLE 5

A pBR322-derived expression plasmid (Pint-γ-tx B4) was used which contained a tryptophan promoter (trp) sequence and an XbaI site 3' to a Shine/Delgarno sequence followed by a structural gene coding for another polypeptide. The extraneous polypeptide was excised and the cGH gene was inserted by a process involving deletion from the sequence set out in Example 4 of the 5' untranslated region and a 78 base pair 5' region coding for the endogenous 25 amino acid leader sequence and the initial threonine residue of the mature polypeptide. The 3' untranslated region was eliminated in part and suitable steps were taken to provide an initial ATG and bases allowing insertion into the XbaI site of the expression vector which follows the trp promoter sequence. The specific procedures for manipulation of the cDNA sequence and for construction of the plasmid are set out in co-owned, co-pending U.S. patent application Ser. No. 445,986 by co-inventor L. Souza, filed Dec. 1, 1982.

After transformation clones were screened for containing a complete cGH coding region by digestion with XbaI and BamHI. The plasmid from one clone, designated cGH-T21, was transformed into $E.\ coli$ K-12 strain C600 (A.T.C.C. 39182) for expression analysis.

The following example is directed to transforming $E.\ coli$ with the plasmid vector to secure expression of the desired polypeptide (i.e., [Met$^{-1}$, des-Thr$^1$]cGH) in bacterial cells.

EXAMPLE 6

Cells of $E.\ coli$ K-12 strain c600 (A.T.C.C. 39182) containing the cGH expression plasmid cGH-T21 are grown in M9 minimal salts supplemented with 0.4% glucose, 1 mM MgSO$_4$, 0.1 mM CaCl$_2$, 5 mg/ml casamino acids and 10 μg/ml thiamine in a 37° C. shaker to an O.D. (A$_{600}$) of 1. At this point, 15 ml of cells are treated with 3-Indoleacrylic acid (final conc. 10 μg/ml) and allowed to continue to shake at 37° C. for 1 hour. 10 ml cells are then pelleted at approximately 4,000 xg in a Beckman J-6 and resuspended in 0.5 ml of a Tris-sucrose-lysozyme buffer (Goeddel, et al., Nature, 281, 544–548 [1981]) containing, in addition, 0.05% sodium dodecyl sulfate and 1 mM phenylmethylsulfonylfluoride. The cells are then placed on ice for 30 minutes after which they are treated with 0.11 ml of a DNase buffer and 10 μg of DNase I (Worthington) as described in Goeddel, et al. The supernate is then spun at 12,000×g for 15 minutes in an Eppendorf microfuge and the supernate is decanted into a tube containing 25 μl of 10% Triton X-100. The sample is then stored on ice until it is subjected to an RIA as described in Example 8.

The following example relates to biochemical similarity of microbially-produced chicken species avian growth hormone according to the invention and growth hormone purified from chicken pituitary glands.

EXAMPLE 7

Chicken growth hormone purified from pituitary glands exhibits a molecular weight (MW) of approximately 24,000 as measured by SDS-Polyacrylamide Gel Electrophoresis (SDS-PAGE). The MW of the microbially-produced avian growth hormone of the invention was determined by SDS-PAGE of $^{35}$S-methionine ($^{35}$S-met) labeled maxicells (CSR603) harboring plasmid, cGH-T21. Briefly, the procedure involves growing 10 mls of CSR603 (cGH-T21) in K-media [Rupp, et al., $J.Mol.Biol.$, 61, pp. 25–44 (1971)] to a concentration of 2×10$^8$ cells/ml. 5 ml of cells are then irradiated in a 60 mm petri dish on a shaker platform with a UV dose of 1–5 J/m$^2$. The cells are then allowed to shake for one hour at 37° C., at which point cycloserine is added at 100 μg/ml. The cultures remain shaking for an additional 8–12 hours. Cells are collected by centrifugation and washed twice with Herschey salts [(Worcel, et al., $J.Mol.Biol.$, 82, pp. 91–105 (1974)]. Cells are resuspended in 2.5 ml of Herschey media and incubated at 37° C. with aeration for one hour. One milliliter of cells is then placed in a 50 ml polypropylene tube with 25 μCi of $^{35}$S-met (New England Nuclear) and 10 μg of 3-Indoleacrylic acid and then incubated for another hour at 37° C. Finally, cells are harvested, lysed and analysed by SDS-PAGE and autoradiography. This procedure had been designed so that nearly all the labeled $^{35}$S-met is incorporated into plasmid encoded gene products. [Sancar, et al., $J.\ Bacteriol.$, 137, p. 692 (1979)].

Two protein bands were detected after autoradiography of the gel. One protein, β-lactamase with a MW of 30,000 is present in all cultures resistant to ampicillin and containing pBR322 derived plasmids. A second protein of MW 24,000 is seen only in cultures containing the plasmid (cGH-T21) encoding the cGH gene. The MW of the microbially-produced avian growth hormone is thus similar to that found for the natural growth hormone isolated from chicken pituitary tissue.

The following example describes a sequential competition radioimmunoassay employing the avian growth hormone polypeptide produced in cells transformed with cGH-T21.

EXAMPLE 8

The bacterial lysate of Example 6 including chicken growth hormone expressed in *E. coli* cells upon transformation with plasmid cGH-T21 was assayed using a sequential competition radioimmunoassay [Zettner, et al., *Clin. Chem.*, 20, pp. 5-14 (1979)].

Purified ovine growth hormone ("oGH") is radioiodinated for use as tracer in this assay using a modification of the chloramine-T reaction procedure described by Hunter and Greenwood, *Nature*, 194, pp. 495-496 (1962). Briefly, the procedure involves combining 10 $\mu$g of oGH in 10 $\mu$l of 0.05M bicarbonate buffer, pH 9.2, 50 $\mu$g chloramine T, and 500 $\mu$Ci of sodium $^{125}$I (approximately 17 Ci/mg) (New England Nuclear) in 50 $\mu$l of 0.2M tris-HCl, pH 7.2, 0.002M EDTA, and incubating for 1 minute at room temperature. Sodium metabisulfite (500 $\mu$g) is added to terminate the reaction and the mixture is loaded onto a 28 ml Sephadex G75 column previously washed with 0.1M phosphate saline (pH 8.0), 2% BSA, and 0.1M phosphate saline (pH 8.0), 0.1% BSA. Four 25-drop fractions are collected from the column and then 45-60 ten drop fractions.

Selected fractions containing radiolabelled material are tested for immune precipitability using the procedure of Keshet, et al., *Nucleic Acids Research*, 9, pp. 19-30 (1981). In this procedure, 2.5 $\times 10^4$ cpm of iodinated oGH is incubated with $1 \times 10^{-4}$ to $2 \times 10^{-4}$ dilutions of rabbit anti-oGH in 0.5M Tris HCl (pH 8.9), 2.0% BSA, 0.1% Triton X-100, 0.1% SDS, for 2 hours at room temperature. Twenty microliters of 10% w/v formalin-fixed *Staphylococcus aureus* pre-washed with RIA buffer is then added and the mixture incubated for 20 minutes at room temperature. Immune precipitates are collected by centrifugation (12,000$\times$g for 3 min.) and washed 3 times in RIA buffer before counting.

In these reactions, a fixed amount of $^{125}$I-labelled oGH reacts with limiting amounts of anti-oGH or anti-cGH to produce immune complexes of I$^{125}$-oGH: anti-oGH. These immune complexes are then precipitated by the *S.aureus*. Unbound $^{125}$I-labelled oGH remains in solution.

The most immune-precipitable column fractions are then used to construct a serum dilution curve using the same procedure as above, but employing serum dilutions over the range of $1 \times 10^{-3}$ to $1 \times 10^{-6}$. The serum dilution giving half maximal precipitation of $2.5 \times 10^4$ cpm of labelled oGH is used in subsequent competition radioimmunoassays.

In those assays, $1 \times 10^{-6}$ to $1 \times 10^{-10}$ g of purified oGH or $10^0$ to $10^{-2}$ dilutions of bacterial lysates of Example 7 containing oGH are pre-incubated with the appropriate dilution of anti-oGH or anti-cGH for 2 hours at room temperature, at which time $2.5 \times 10^{-4}$ to $3.5 \times 10^{-4}$ cpm of $^{125}$I-oGH is added and the subsequent reactions, centrifugation and washing are accomplished as described above.

When the bacterial lysate cGH is added to a fixed amount of anti-oGH or anti-cGH, the appropriate immune complexes are formed. The fixed amount of labelled oGH added to the reaction mixture complexes with any anti-oGH or anti-cGH not previously bound to the bacterial lysate cGH competitor. The amount of radio-activity in the resulting precipitate is inversely proportional to the amount of cGH competitor present in the sample.

This immunoassay thus indicates that the bacterial lysates of Example 6 do, indeed, contain the DNA sequence capable of synthesizing a polypeptide exhibiting one or more of the biological characteristics of chicken growth hormone including the ability of the polypeptide to form antigen-antibody complexes with antibodies to homologous and heterologous species growth hormone.

The following example describes an in vitro manufactured portion of a cGH gene sequence which incorporates *E.coli* preference codons and restriction sites for vector insertion.

EXAMPLE 9

In an effort to increase expression of the cGH gene, a nucleotide sequence coding for the first third of the gene has been synthesized in vitro as a "replacement" for approximately the initial one-third of the cDNA-derived gene. The purpose of the synthesis is to place an XbaI site sticky end three nucleotides upstream of an introduced ATG [Met$^{-1}$] transcription start site, to have an Eco RI site upstream from (and partially overlapping) the naturally-occurring TaqI site, and to have a TaqI site sticky end for splicing the gene back together at the naturally occurring TaqI site. The synthesis is also undertaken to obtain optimal codon usage for expression in *E. coli* and have an adenine- and thiamine-rich region for the first few amino acids of the sequence. Because of the frequency of prolines and alanines in the sequence, however, it is difficult to get an AT-rich start sequence. The nucleotide sequence which maximally satisfies these conditions is the following:

```
              10          20          30          40
    XbaI
5'- CTAGAGAATGT  TTCCAGCTAT  GCCTCTGTCT  AATCTGTTTG
3'-     TCTTACA  AAGGTCGATA  CGGAGACAGA  TTAGACAAAC 50          60          70          80          90
    CAAACGCTGT  TCTGCGTGCA  CAGCATCTGC  ATCTGCTGGC  CGCTGAAACT
    GTTTGCGACA  AGACGCACGT  GTCGTAGACG  TAGACGACCG  GCGACTTTGA
```

```
        1
        0
        0
TATAAAGAAT   T-3'
ATATTTCTTA   AGC-5'
    EcoRI    TaqI
```

It may be noted that the above sequence may be inserted in plasmid cGH-T21 (from which an XbaI/-TaqI fragment has been excised to provide for microbial expression of [Met$^{-1}$, des-Thr$^1$]cGH polypeptide. If [Met$^{-1}$]cGH production is desired, the synthetic fragment is manufactured as previously described with a threonine-specifying codon adjacent (3') to the ATG codon specifying methionine.

The following example relates to manipulations leading to development of another expression vector successfully employed to secure high levels of expression of a polypeptide having the biochemical and immunological properties of avian growth hormone, specifically [Met$^{-1}$, des-Thr$^1$]cGH polypeptide.

EXAMPLE 10

The manipulations herein-described involved use of plasmid pCFM414 which is the subject of co-owned, co-pending U.S. patent application Ser. No. 521,964, filed Aug. 10, 1983, by C. F. Morris, entitled "DNA Vector". The disclosure of said application are specifically incorporated by reference herein. Briefly noted, plasmid pCFM414 (A.T.C.C. 40076) includes a temperature-sensitive mutation in the copy control region. Upon transformation with this vector, host cell cultures grown at 30° C. will have a low number of copies of the plasmid. The plasmid copy number increases fifty-fold or more (i.e., "runs away") within the host cells upon elevation of the culture temperature above 34° C. Growth at 37° C. will ordinarily be lethal to the cells but prior to cell death there is an opportunity for multiple transcriptions of plasmid DNA.

The specific manipulations involved in construction of a vector using A.T.C.C. 40076 were as follows. Plasmid cGH-T21 (in A.T.C.C. 39182) was digested with restriction endonucleases EcoRI and NcoI, thereby excising a fragment containing a trp promoter originally present in Pint-γ-txB4 followed by the cGH polypeptide coding region and a few base pairs from the untranslated 3' region of the gene (See Table I).

Plasmid pCFM414 was digested with EcoRI and NcoI and the large fragment isolated. The EcoRI/NcoI fragment from cGH-T21 was ligaed to the large EcoRI/NcoI fragment of pCFM414 to yield plasmid 414cGH-T2. Growth of E.coli AM7 cells transformed with plasmid 414cGH-T2 resulted in production of the desired polypeptide in low yields which were about four-fold greater than provided by cGH-T21 in E.coli C600 cells.

The following example describes procedures for obtaining and sequencing DNA for turkey species avian growth hormone.

EXAMPLE 11

Another avian growth hormone polypeptide coding DNA sequence, for turkey growth hormone ("tGH"), was prepared by employing the procedures of Examples 1 through 4 above, with two alterations in procedure: (1) turkey pituitaries were used in the procedure of Example 1; and (2) a cGH probe (i.e., a BamHI/NcoI fragment as shown in Table I) was employed in the procedure of Example 3. One clone was selected for further characterization and sequence analysis following the performance of procedures in Example 3. Sequencing of the recombinant tGH DNA obtained by the procedure of Example 3 was accomplished by the dideoxy method of Sanger, et al., *PNAS*, 74, pp. 5463-5467 (1977).

The single-stranded DNA phage M-13 was used as a cloning vector for supplying single-stranded DNA templates from the double-stranded cDNA clones. The Sanger, et al. method revealed the sequence for the tGH protein coding DNA single strand in M-13. This sequence, like that of cGH, includes the polypeptide coding region containing a single BamHI recognition site; an approximately 75 base pair sequence 5' to the protein coding region, which sequence presumptively codes for a 25 amino acid leader region; and 3' and 5' untranslated regions. The polypeptide-coding DNA sequence is set out in Table II below with its accompanying amino acid sequence:

TABLE II

5'-CCTGGATGAAAGGAGGAAACGCTCAAGCAACACCCGAGCACCTCTCCTGGCGGGA

| −25 | | | | | −20 | | | | | | | | |
|---|---|---|---|---|---|---|---|---|---|---|---|---|---|
| Met | Ala | Pro | Gly | Ser | Trp | Phe | Ser | Pro | Leu | Leu | Ile | Ala | Val |
| ATG | GCT | CCA | GGC | TCG | TGG | TTT | TCT | CCT | CTC | CTC | ATT | GCT | GTG |

| | −10 | | | | | | | | | | 1 | | |
|---|---|---|---|---|---|---|---|---|---|---|---|---|---|
| Val | Thr | Leu | Gly | Leu | Pro | Gln | Gly | Ala | Ala | Ala | Thr | Phe | Pro |
| GTC | ACG | CTG | GGA | CTG | CCC | CAG | GGA | GCT | GCT | GCC | ACC | TTC | CCT |

| | | | | | | 10 | | | | | | | |
|---|---|---|---|---|---|---|---|---|---|---|---|---|---|
| Thr | Met | Pro | Leu | Ser | Asn | Leu | Phe | Thr | Asn | Ala | Val | Leu | Arg |
| ACC | ATG | CCC | CTC | TCC | AAC | CTG | TTC | ACC | AAC | GCT | GTG | CTG | AGG |

| | | 20 | | | | | | | | | | 30 | |
|---|---|---|---|---|---|---|---|---|---|---|---|---|---|
| Ala | Gln | His | Leu | His | Leu | Leu | Ala | Ala | Glu | Thr | Tyr | Lys | Glu |
| GCT | CAG | CAC | CTC | CAC | CTC | CTG | GCT | GCT | GAG | ACA | TAC | AAA | GAG |

| | | | | | | | 40 | | | | | | |
|---|---|---|---|---|---|---|---|---|---|---|---|---|---|
| Phe | Glu | Arg | Thr | Tyr | Ile | Pro | Glu | Asp | Gln | Arg | Tyr | Thr | Asn |
| TTC | GAA | CGC | ACC | TAT | ATT | CCG | GAG | GAC | CAG | AGG | TAC | ACC | AAC |

TABLE II-continued

| Lys | Asn | Ser | Gln | Ala | Ala | Phe | Cys | Tyr | Ser | Glu | Thr | Ile | Pro |
|---|---|---|---|---|---|---|---|---|---|---|---|---|---|
| AAA | AAC | TCC | CAG | GCT | GCA | TTT | TGT | TAC | TCA | GAA | ACC | ATC | CCA |
| 60 | | | | | | | | | | 70 | | | |
| Ala | Pro | Thr | Gly | Lys | Asp | Asp | Ala | Gln | Gln | Lys | Ser | Asp | Met |
| GCT | CCC | ACA | GGG | AAG | GAT | GAT | GCC | CAG | CAG | AAA | TCG | GAC | ATG |
| Glu | Leu | Leu | Arg | Phe | Ser | 80 Leu | Val | Leu | Ile | Gln | Ser | Trp | Leu |
| GAG | CTG | CTT | CGG | TTT | TCA | CTG | GTT | CTC | ATC | CAG | TCC | TGG | CTG |
| Thr | Pro | 90 Met | Gln | Tyr | Leu | Ser | Lys | Val | Phe | Thr | Asn | 100 Asn | Leu |
| ACC | CCC | ATG | CAA | TAC | CTA | AGC | AAG | GTG | TTC | ACA | AAC | AAT | TTG |
| Val | Phe | Gly | Thr | Ser | Asp | Arg | Val | 110 Phe | Glu | Lys | Leu | Lys | Asp |
| GTT | TTC | GGC | ACC | TCA | GAC | AGA | GTG | TTT | GAG | AAA | CTA | AAG | GAC |
| Leu | Glu | Glu | Gly | 120 Ile | Gln | Ala | Leu | Met | Arg | Glu | Leu | Glu | Asp |
| CTG | GAA | GAA | GGG | ATC | CAA | GCC | CTG | ATG | AGG | GAG | TTG | GAG | GAT |
| 130 Arg | Ser | Pro | Arg | Gly | Pro | Gln | Leu | Leu | Arg | 140 Pro | Thr | Tyr | Asp |
| CGC | AGC | CCG | CGG | GGC | CCG | CAG | CTC | CTC | AGA | CCC | ACC | TAC | GAC |
| Arg | Phe | Asp | Ile | His | Leu | 150 Arg | Ser | Glu | Asp | Ala | Leu | Leu | Lys |
| AGG | TTC | GAC | ATC | CAC | CTG | CGC | AGC | GAG | GAC | GCC | CTG | CTG | AAG |
| Asn | Tyr | Gly | Leu | Leu | Ser | Cys | Phe | Lys | Lys | Asp | Leu | 170 His | Lys |
| AAC | TAC | GGC | TTG | CTG | TCC | TGC | TTC | AAG | AAG | GAC | CTG | CAC | AAA |
| Val | Glu | Thr | Tyr | Leu | Lys | Val | Met | 180 Lys | Cys | Arg | Arg | Phe | Gly |
| GTG | GAG | ACC | TAC | CTG | AAG | GTG | ATG | AAG | TGC | CGG | CGC | TTC | GGG |
| Glu | Ser | Asn | Cys | 190 Asn | Ile | OP | | | | | | | |
| GAG | AGC | AAC | TGC | AAC | ATC | TGA | GGCTCTCTGTGCCCCCATGG-3' | | | | | GCC | |

It will be apparent from comparison of the above sequence to the Table I sequence of cDNA derived from chicken pituitary cells that in a number of instances alternative codons specifying the same amino acid are present and that the tGH cDNA sequence specifies a polypeptide with substantial homology to that specified by the cGH cDNA sequence. One hundred and eighty-five of the one hundred ninety-one amino acid residues are identical. In the sequence specified by the tGH gene, threonine is specified at residue number 4, rather than an alanine as in the cGH gene. In a like manner, threonine rather than alanine is specified at position number 11; methionine rather than valine is specified at position number 90; arginine rather than lysine is specified at position number 144; serine rather than asparagine is specified at position 151; and asparagine rather than threonine is specified at position number 190. The amino acids specified for the "leader" sequence are identical except for the presence of glycine at position 4, rather than glutamine.

To secure direct expression of the tGH cDNA sequence in a microbial host, the tGH coding region should be provided with an initial ATG codon 3' to the codon for the amino terminal threonine residue and the sequence inserted in a transformation vector at a site under control of a suitable promoter/regulator DNA sequence. An expression vector similar to that constructed in Example 5 for cGH can be employed to express tGH in a microbial host.

Similarly, a "replacement" nucleotide sequence for the first third of the tGH-derived gene may be constructed and employed as in Example 9 to place selected restriction endonuclease enzyme recognition sites in the sequence, to obtain optimal codon usage for expression in E. coli, and to have an adenine- and thiamine-rich start sequence.

While the foregoing illustrative examples relate generally to microbial expression of cGH by bacterial cells transformed with a bacterially-derived vector, it will be apparent that expression in yeast and other microorganism cells is also contemplated, as is the development of DNA sequences having manufactured portions including codons which are the subject of optimal expression in the selected host. Yeast expression, for example, would involve vector development in the context of the requirements peculiar to the synthesis of protein in yeast host cells, e.g., use of DNA vectors capable of autonomous replication in yeast, use of yeast promotor/regulator regions, and the like. See, e.g., Valenzuela, et al., Nature, 298, pp. 347-350 (1982) relating to expression of hepatitis B surface antigen in yeast cells.

As previously noted, polypeptide products of the invention are expected to have commercial utility in animal husbandry procedures involving, e.g., continuous low level delivery of products to poultry as a feed or water supplement or as active components delivered by means of a slow dissolving (or slow ingredient-releasing) subcutaneous implant. Such delivery systems would be particularly advantageous in treatment of young fowl during early growth stages.

Numerous other modifications and variations in the invention are expected to occur to those skilled in the art upon consideration of the foregoing description. Consequently, only such limitations as appear in the appended claims should be placed on the invention.

What is claimed is:

1. A purified and isolated DNA sequence coding for expression of chicken growth hormone polypeptide.
2. A purified and isolated DNA sequence coding for expression of turkey growth hormone polypeptide.

* * * * *